United States Patent
Staton et al.

(10) Patent No.: US 10,432,900 B2
(45) Date of Patent: Oct. 1, 2019

(54) FIXTURE

(71) Applicant: NEWTONOID TECHNOLOGIES, L.L.C., Liberty, MO (US)

(72) Inventors: Fielding B. Staton, Liberty, MO (US); David Strumpf, Columbia, MO (US)

(73) Assignee: Newtonoid Technologies, L.L.C., Liberty, MO (US)

( * ) Notice: Subject to any disclaimer, the term of this patent is extended or adjusted under 35 U.S.C. 154(b) by 0 days.

(21) Appl. No.: 16/272,749

(22) Filed: Feb. 11, 2019

(65) Prior Publication Data

US 2019/0174104 A1    Jun. 6, 2019

Related U.S. Application Data

(63) Continuation of application No. 15/939,106, filed on Mar. 28, 2018, now Pat. No. 10,205,919.

(Continued)

(51) Int. Cl.
| | |
|---|---|
| G06F 3/01 | (2006.01) |
| G03B 21/14 | (2006.01) |
| H04N 9/31 | (2006.01) |
| F21S 8/02 | (2006.01) |
| G06F 16/50 | (2019.01) |
| G03B 17/54 | (2006.01) |
| G03B 17/56 | (2006.01) |
| A61L 9/12 | (2006.01) |
| G09F 19/18 | (2006.01) |
| F21W 131/401 | (2006.01) |
| G09F 27/00 | (2006.01) |

(Continued)

(52) U.S. Cl.
CPC .............. *H04N 9/3141* (2013.01); *A61L 9/12* (2013.01); *F21S 8/02* (2013.01); *G03B 17/54* (2013.01); *G03B 17/561* (2013.01); *G03B 21/14* (2013.01); *G03B 21/145* (2013.01); *G06F 3/01* (2013.01); *G06F 16/50* (2019.01); *H04N 9/3194* (2013.01); *F21S 8/026* (2013.01); *F21V 33/0096* (2013.01); *F21W 2131/103* (2013.01); *F21W 2131/401* (2013.01); *F21Y 2115/10* (2016.08); *G09F 19/18* (2013.01); *G09F 27/005* (2013.01)

(58) Field of Classification Search
CPC . G06F 3/01; G06F 3/011; G06F 3/017; G03B 21/14; H04N 9/3194; H04N 9/3147
See application file for complete search history.

(56) References Cited

U.S. PATENT DOCUMENTS

| | | | |
|---|---|---|---|
| 6,843,694 B2 | 1/2005 | Simmons | |
| 10,205,919 B2 * | 2/2019 | Staton | G06F 3/01 |

(Continued)

OTHER PUBLICATIONS

PCT Appln. No. PCT/US2018/024963, International Search Report and Written Opinion, dated Jun. 11, 2018, 14 pages.

(Continued)

*Primary Examiner* — Ryan D Howard

(74) *Attorney, Agent, or Firm* — Lathrop Gage L.L.P.

(57) ABSTRACT

A fixture includes a housing having an output device, at least one sensor, and a projector for projecting image data. The fixture further includes a fixture computing system that is communicatively coupled to the output device, the sensor, and the projector and includes a processor, and non-transitory computer memory having programming for receiving information from the at least one sensor and causing the projector to project the image data.

12 Claims, 12 Drawing Sheets

Related U.S. Application Data

(60) Provisional application No. 62/477,655, filed on Mar. 28, 2017.

(51) Int. Cl.
*F21V 33/00* (2006.01)
*F21W 131/103* (2006.01)
*F21Y 115/10* (2016.01)

(56) References Cited

U.S. PATENT DOCUMENTS

| | | |
|---|---|---|
| 2008/0106422 A1 | 5/2008 | Sparks et al. |
| 2012/0269399 A1 | 10/2012 | Anderson et al. |
| 2013/0063702 A1 | 3/2013 | Nemeth et al. |
| 2015/0087278 A1* | 3/2015 | Kim .................... H04L 12/2818 455/414.1 |
| 2015/0382434 A1 | 12/2015 | Noesner et al. |
| 2016/0241823 A1* | 8/2016 | Blaser, Jr. ............ H04N 9/3144 |

OTHER PUBLICATIONS

Aura Lighting, Aura Light, Sustainable Lighting for Business, dated Feb. 21, 2017—Applicant Admitted Prior Art.

* cited by examiner

FIXTURE

CROSS-REFERENCE TO RELATED APPLICATIONS

This application is a continuation of U.S. patent application Ser. No. 15/939,106, filed Mar. 28, 2018, which is pending and claims priority to U.S. Provisional Patent Application No. 62/477,655, filed Mar. 28, 2017, the entireties of both of which are incorporated by reference herein.

BACKGROUND

Fixtures are a staple in and around nearly every building in industrialized nations. Lighting fixtures are obviously useful for illuminating rooms. Other fixtures are also widely used, including fixtures for fans, among others. However, technology surrounding fixtures has remained relatively unchanged for a number of years. Because fixtures are located in nearly every room of a building, as well as many areas outside of a building, there is significant opportunity to incorporate fixtures as a part of an overall system having increased abilities to interact with subjects (e.g., humans, animals, and objects).

SUMMARY

The following presents a simplified summary of the invention in order to provide a basic understanding of some aspects of the invention. The summary is not an extensive overview of the invention. It is not intended to identify critical elements of the invention or to delineate the scope of the invention. Its sole purpose is to present some concepts of the invention in a simplified form as a prelude to the more detailed description that is presented elsewhere.

In one embodiment, a fixture includes a housing having an output device, at least one sensor, and a projector for projecting image data. The fixture further includes a fixture computing system that is communicatively coupled to the output device, the sensor, and the projector and includes a processor, and non-transitory computer memory having programming for receiving information from the at least one sensor and causing the projector to project the image data.

In another embodiment, a fixture system includes a fixture, a fixture computing system, and a first remote response module. The fixture has a housing with at least one sensor and a projector for selectively projecting image data onto a surface. The fixture computing system is communicatively coupled to the sensor and the projector, and includes at least a processor, and non-transitory computer memory comprising programming for receiving information from the at least one sensor; transmitting the sensor information over a network; determining the presence of a situation; and retrieving the image data from a database for display by the projector. The first remote response module has a first remote response computing system that is communicatively coupled to the fixture computing system. The first remote response computing system similarly has a processor, and non-transitory computer memory with programming for receiving the sensor information from the fixture computing system and activating the remote response module.

In still another embodiment, a fixture system includes a housing with a light and a projector for projecting image data onto a surface. The system further includes a fixture computing system having a processor, and non-transitory computer memory comprising programming for causing the projector to project the image data.

DETAILED DESCRIPTION

Embodiments of fixtures having increased functionalities as part of an overall communications system are described herein. As will be described in greater detail below, in one embodiment, a fixture may be a stand-alone device, generally configured to interact with a system for providing information to a user via a display. In another embodiment, a fixture may be further configured to interact with a user to provide a user-specific output in accordance with the system with which it is associated. While specific embodiments of various fixtures are described in detail herein, it shall be understood that the underlying invention described herein can be incorporated for use with any fixture which may be found in or around a location.

Figure 1:
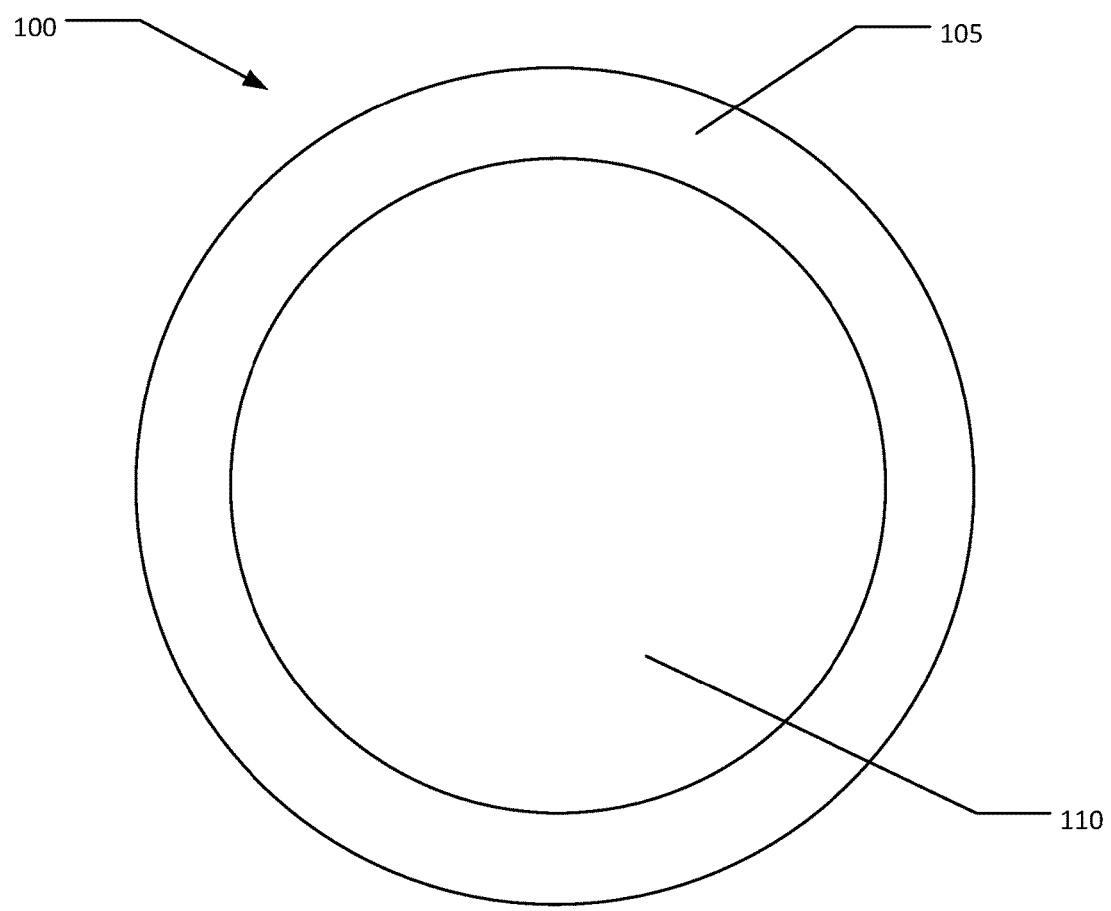
FIG. 1 is a bottom view of a fixture according to an embodiment of the invention.
Figure 2:
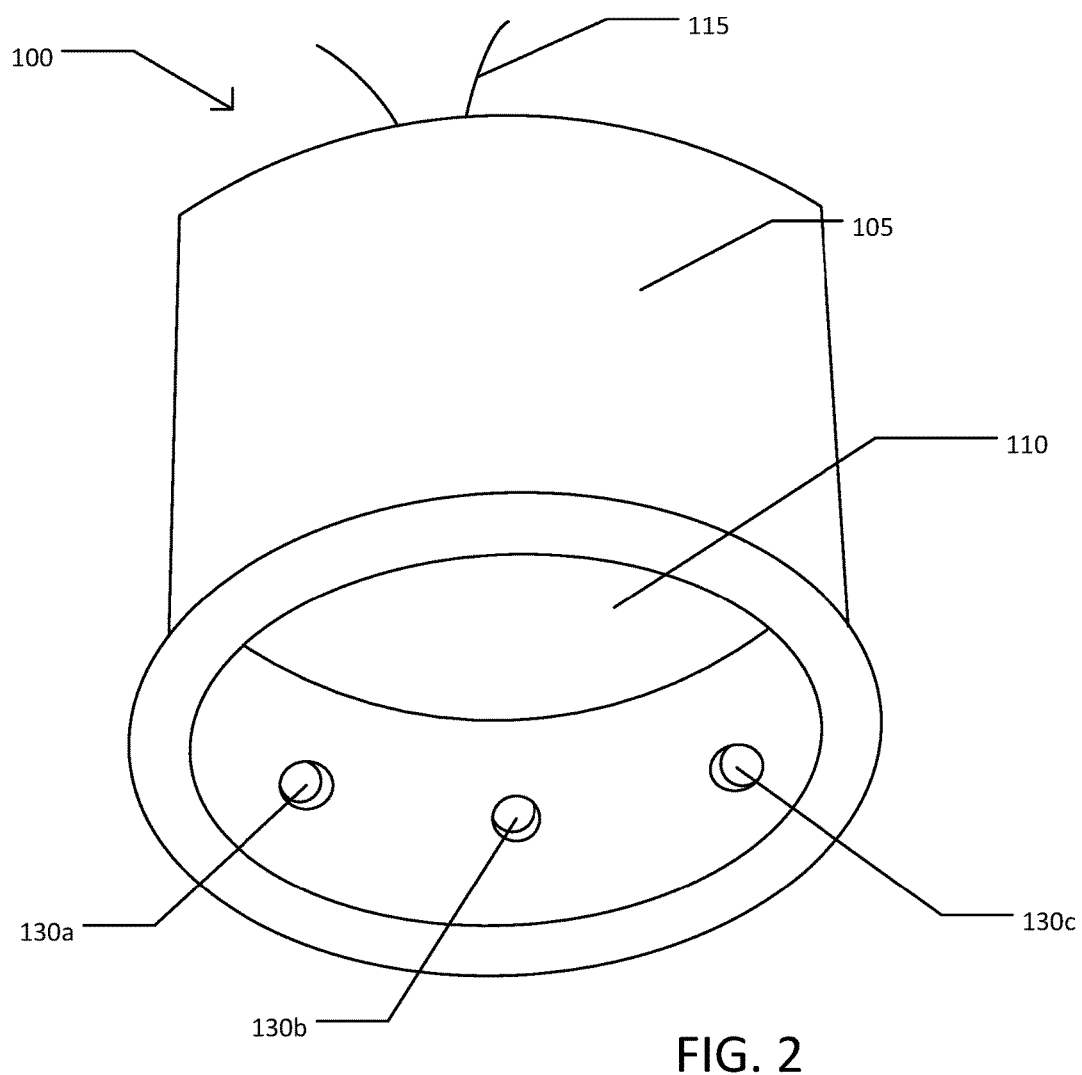
FIG. 2 is a perspective view of the fixture of FIG. 1.

FIGS. 1-2 illustrate a fixture 100 according to one embodiment of the invention. Here, the fixture 100 is embodied as a can light, such as those typically found in a ceiling of a building. Here, the fixture 100 includes a housing 105 and a light 110. The light 110 may, in embodiments, be an LED light, although other types of lights may additionally or alternately be appropriate. The housing 105 and/or the light 110 may be equipped with wiring 115 for receiving and/or transferring power as described below. The housing 110 may be equipped with one or more input and/or output devices 130a, 130b, 130c (generally sensors, 130), which are part of a fixture computing device 117 associated with the fixture 100. The fixture computing device 117 may be directly associated with the fixture 100, or may be distributed (i.e., remote) from the fixture 100. In any event, the fixture computing device 117 is communicatively coupled to the fixture 100.

The wiring 115 may include traditional electrical wiring, which may allow the light 110 and/or the fixture computing device 117 to hook into the existing electrical system. Alternately, the wiring 115 may be, for example, light pipes or fiber optics which may receive light from another area in a building in order to power the light 110 and/or the fixture computing device 117. In one embodiment, a sensor 130a may include a light detection and transmission sensor (e.g., one or more solar panels) which may be configured to receive, transduce, and store ambient light energy to provide power to the light 110. Energy from the sensor 130a may be stored (e.g., in a battery, capacitor, etc.) to provide electrical power to the light 110 and/or the fixture computing device 117 during periods of low ambient light exposure (e.g., at night).

Further, the light 110 (and other components) may be controlled via a DIP switch (or other programmable configuration device). As known to those of skill in the art, the DIP switch may allow for remote control of the light without requiring an electrical connection between the light 110 and the on/off switch. This may be particularly advantageous where the wiring 115 includes light pipes and/or fiber optics and is otherwise not dependent on electrical energy. Energy harvesting techniques can be used from the optical pipe system to distribute power to subsystems in select embodiments.

Sensors 130a and 130b may be, for example, a motion detector, proximity sensor, camera, video camera, infrared detector, a receiver, humidity sensor, thermometer, or any other sensor that is now known or later developed. It shall be understood that the sensor 130b may include a plurality of sensors, including but not limited to those listed immediately above. The sensors 130b which may be incorporated into the fixture 100 may be selected based on the location of the fixture 100 and/or the desirable function of the fixture 100. In embodiments, the sensors 130b may optionally be removable and/or exchangeable, to allow a user to customize the fixture 100 according to the user's desires. The sensors 130b may be configured to communicate with the fixture computing device 117 as described in greater detail below.

Figure 4:
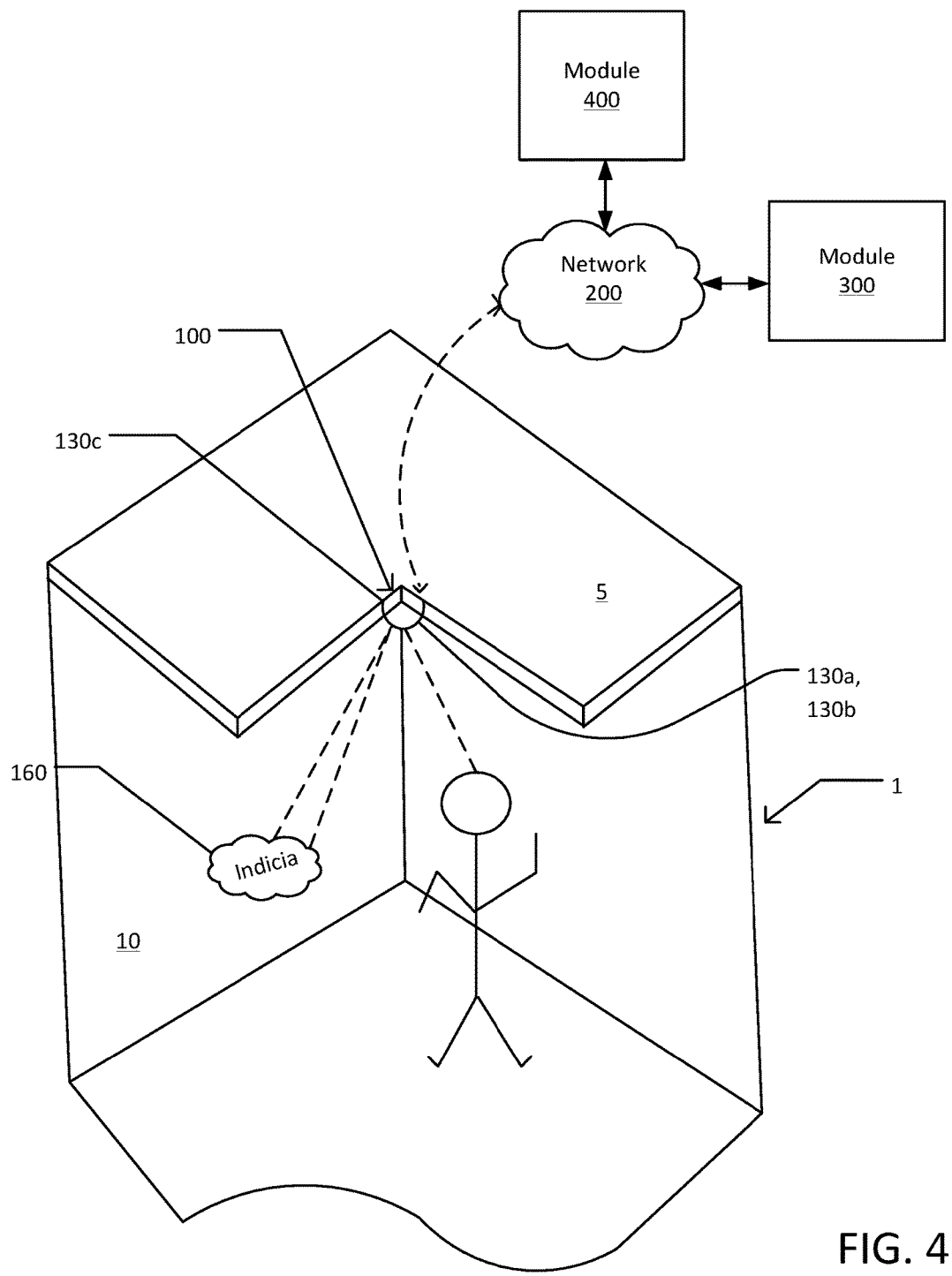
FIG. 4 is a schematic of a system incorporating a fixture according to another embodiment of the invention.
Figure 5:
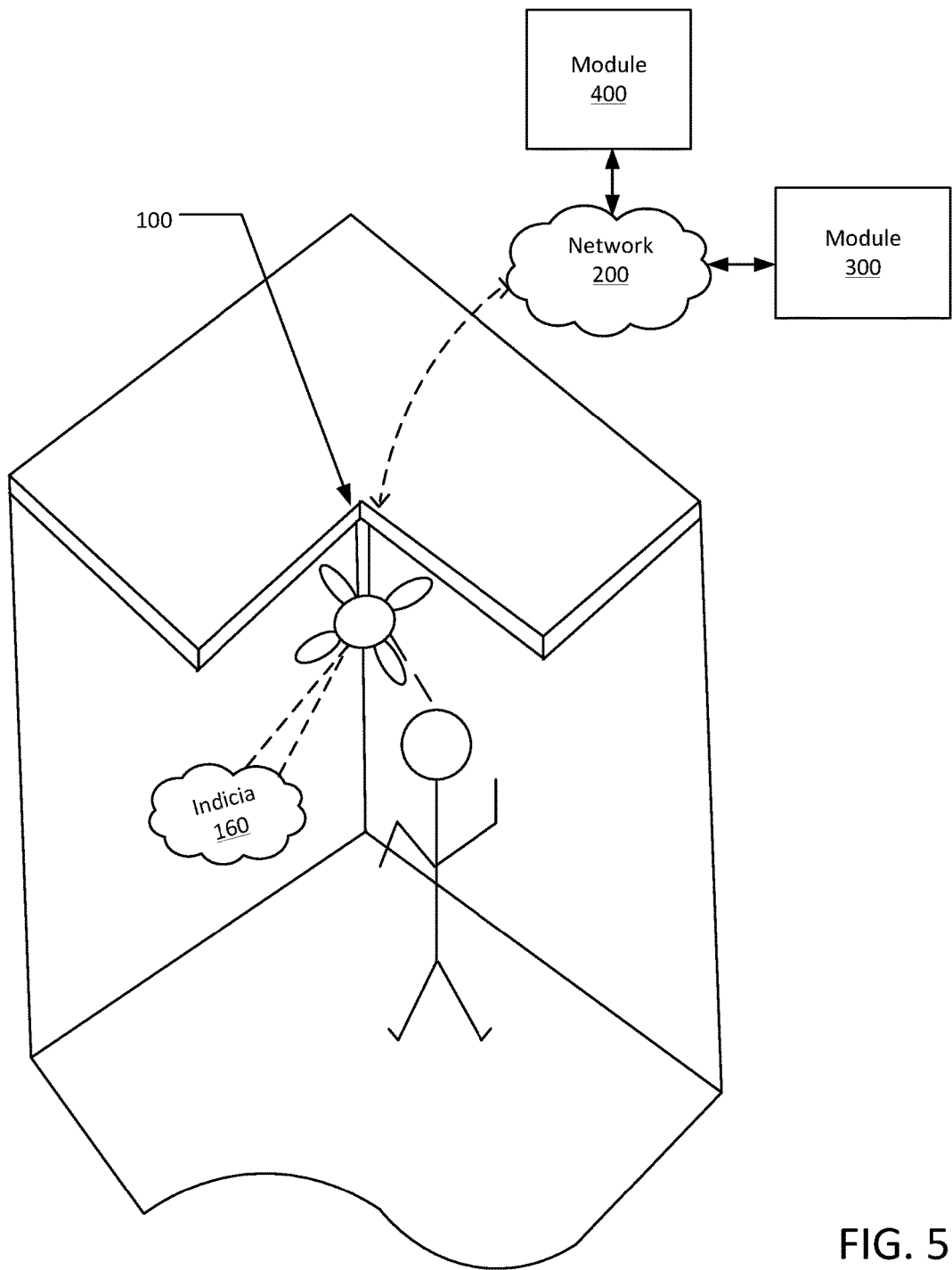
FIG. 5 is a schematic illustrating a system incorporating a fixture according to still another embodiment of the invention.

An output device 130c, such as a projector, may be situated in the housing 110, e.g., along an inner rim of thereof. The projector 130c may be configured to provide display content on a surface near the fixture 100. FIG. 4 shows a schematic illustration of a fixture 100 embodied as a can light disposed in a ceiling 5 of a building 1. FIG. 5 shows a schematic illustration of a fixture 100 embodied in a ceiling fan. In both embodiments, although not necessarily required, the projector 130c of the fixture 100 projects indicia 160 onto the wall 10. In embodiments, multiple projectors 130c may be included in the fixture 100, and indicia 160 may be projected onto multiple surfaces. It shall be understood that the output device 130c may be embodied in a plurality of output devices 130c, including but not limited to a projector, speakers, lights, fragrance delivery systems, noise/vibration canceling propagation devices, radio frequency (RF) repeaters, etc.

Figure 3:
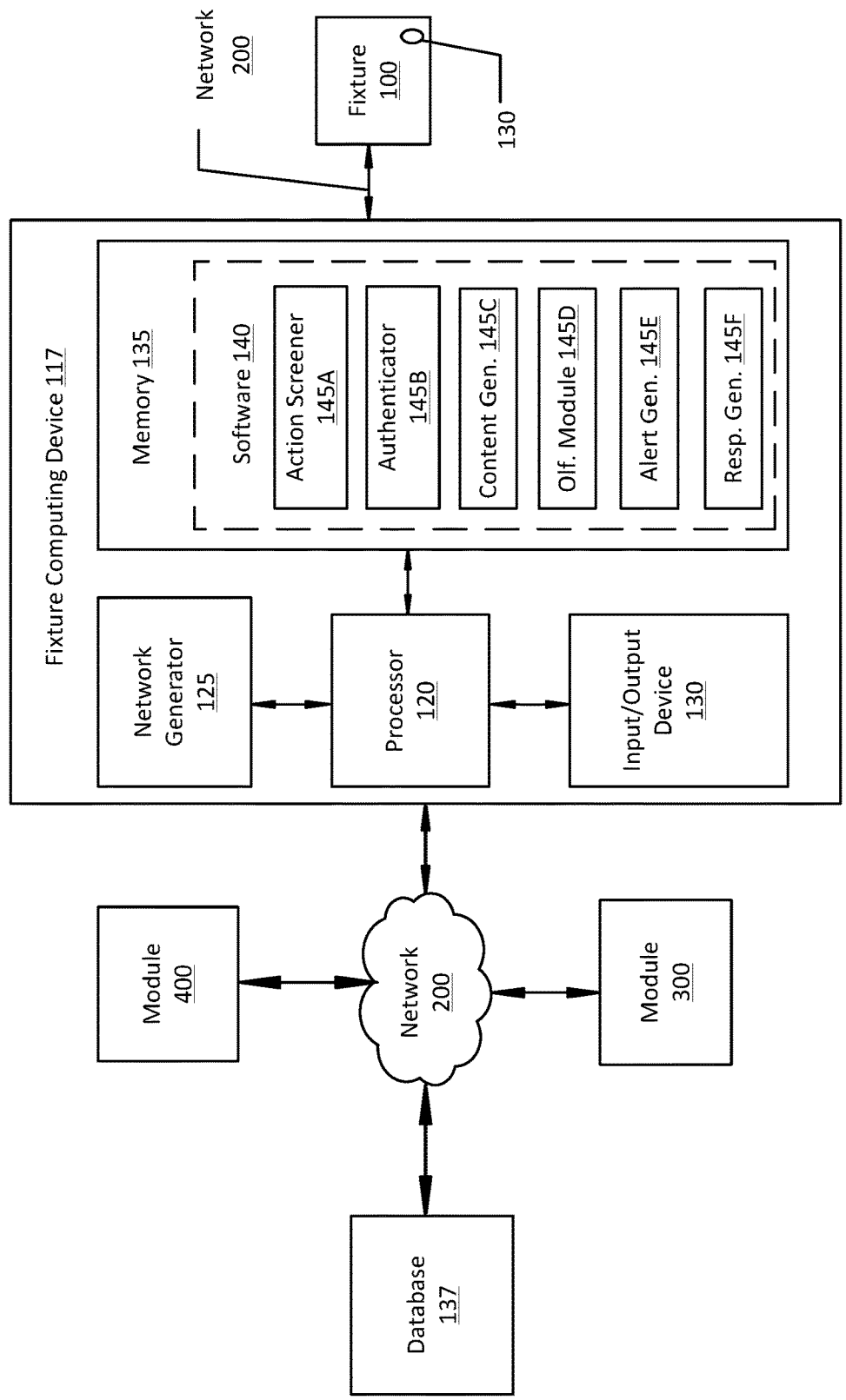
FIG. 3 is a schematic of a system incorporating a fixture according to an embodiment of the invention.

Attention is now directed to FIG. 3, which schematically illustrates a system having an exemplary fixture computing device 117 with analysis and response capabilities. The fixture 100, fixture computing device 117, and other computing devices (or modules 300 and 400) are communicatively coupled (e.g., via wires or wirelessly over a network 200). The fixture computing device 117 includes a processor 120 communicatively coupled to a network interface 125, and memory 135. The sensors 130a, 130b, 130c may be in communication (e.g., via wires or wirelessly over the network 200) with the processor 120. The processor 120 operates software 140 housed in the memory 135.

Processor 120 represents one or more digital processors. In some example embodiments, the processor 120 may be configured through particularly configured hardware, such as an application specific integrated circuit (ASIC), field-programmable gate array (FPGA), etc., and/or through execution of software to perform functions in accordance with the disclosure herein. Network interface 125 may be implemented as one or both of a wired network interface and a wireless network (e.g., Wi-Fi, Internet, Bluetooth, Cellular, etc.) interface, as is known in the art. Memory 135 represents one or more of volatile memory (e.g., RAM) and non-volatile memory (e.g., ROM, EPROM, FLASH, magnetic media, Electrochromic, Active Graphically Encoded Icon (GEI), optical media, chemical, etc.). Although shown within the fixture computing device 117, memory 135 may be, at least in part, implemented as network storage that is external to the fixture 100 and/or the fixture computing device 117, and accessed via network interface 125.

Software 140 may be stored in a transitory or non-transitory portion of the memory 135. Software 140 includes machine readable instructions that are executed by processor 120 to perform the functionality of the computing device 117 as described herein. In the illustrated example, the software 140 contains one or more modes of functionality, including but not limited to an action screener 145A, an authenticator 145B, a primary content generator 145C, an olfaction module 145D, an alert generator 145E, and a response generator 145F, each of which are described in more detail below. The software 140 may contain fewer modes of functionality, depending on the sensors 130. As the sensors 130 receive data, the information may be evaluated by the software 140 to determine what, if any action, by the fixture 100 is desirable.

The authenticator 145B may, in embodiments, communicate with a mobile computer of a user (discussed further below) to verify the identity of the user. For instance, and as discussed below, a user may download a mobile application to allow him to interact with the fixture 100. During the installation process, a unique number associated with the user's mobile computer (e.g., an Android ID, a Google Advertising ID, a Universal Device ID, etc.) may be retrieved and stored (e.g., in cloud storage). When a proximity sensor 130 (see FIG. 1) indicates that a user is proximate (e.g., within 1-5 feet of) the fixture 100, the authenticator 145B may use the network interface 125 to interact with the user's mobile computer (e.g., over Bluetooth Low Energy (BLE) beacons, LIDAR, or other triangulation network techniques) to determine the device ID and/or physical position of the user's mobile computer. It shall be understood that the proximity sensor 130 as well as the user's mobile computer are not limited to traditional devices that exist today and could extend their operation onto (or within) future devices that utilize distributed networking techniques such as Internet of Things (IoT) which may eventually be embedded into objects, animals, and humans. The authenticator may thereafter match the device ID obtained when the user is at the fixture 100 with the device ID retrieved during the mobile application installation, and thereby, identify and authenticate the user. Optionally, the user may engage with the mobile computer and the mobile application to save preferences of the user (e.g., favorite shows, news channels, music, movies, etc.). Where the user has uploaded preferences into the mobile application, and the proximity sensor 130 determines that the user is proximate the fixture 100, the processor 120 may activate the primary content generator, discussed below, to provide the preferred content for the user to see.

The primary content generator 145C may generate content (e.g., indicia 160, see FIG. 4) for display on a surface near the fixture 100. The primary display content 160 may be general content or individualized (i.e., personalized) content. General content, as used herein, may include TV channels, sports games, movies, non-targeted advertisements, etc. Individualized content, as used herein, may include a personalized message, targeted advertising, cryptographic digital ledger (Blockchain), or any other content that is tailored to the particular user near the fixture 100. In an embodiment, when the authenticator does not recognize the user, or preferences have not been uploaded, the content 160 displayed on the display surface may be general content. When a user is near the fixture 100 and his identity is confirmed using the authenticator 145B, the primary content generator 145C may cause the projector 130c to display content 160 that is personalized to that user. For instance, where the user provides his name as part of the installation of the mobile application to interact with the fixture 100 (discussed further below), upon identification of the user at the fixture 100 via the authenticator 145B, the primary content generator 145C may cause the projector 130c to display an individualized message that includes the name of the user. Alternately or in addition, during installation of the mobile application, the user may pick topics that are of interest to the user, and the projector 130c may display personalized content (e.g., targeted advertisements, movie trailers, biometric related data, etc.) in line with the user's preferences. In some embodiments, the personalized content may be dynamic (e.g., where the user used a search engine on the mobile device to search for listings for a new vehicle within the last hour, the primary content generator 145C, upon communication of the mobile device with the software 140, may display advertisements for new vehicles). The projector 130c may thus, in embodiments, provide the user a personalized and immersive experience via the fixture 100.

The alert generator 145E may generate a second content for interacting with the user. For example, in some embodiments, the alert generator 145E may cause an alert (specifically, a sound or flashing lights via an appropriate output device 130) to be generated when a sensor 130 indicates the presence of possible harm. Additionally, a display 160 may be displayed (e.g., via the projector 130c) to alert the user to the possible danger. For example, the fixture 100 may include an infrared sensor 130 for detecting heat patterns. If the infrared sensor 130 detects the presence of a hot spot, for example, the sensor 130 may, in conjunction with the processor 120 and the alert generator, cause a display to appear on a surface near the fixture (e.g., "FIRE—EXIT THE BUILDING IMMEDIATELY"). At the same time, the fixture 100 may optionally activate one or more output devices 130 (e.g., lights and/or sound) to provide an auditory alert to nearby persons. Additionally, the fixture 100 may activate, via the response generator 145F, one or more remote devices, here, sprinklers (represented by module 300 in FIG. 4) to address the fire. It shall thus be understood that the sprinkler (and any other remote module 300, as discussed herein) may be equipped with a network interface and processor for communicating over the network 200 with the fixture computing device 117 for the purpose of receiving instructions from the fixture computing device 117 in response to information received from the one or more sensors 130.

The olfaction module 145D may utilize olfactory sensors to detect the presence of an undesirable scent near the fixture 100. Upon determining the presence of an undesirable scent, the olfaction module may, in conjunction with the processor 120, cause a predetermined amount of perfume to be sprayed into the room. The olfaction module 145D may be configured to routinely run, for example, every 20 minutes, 30 minutes, 45 minutes, 60 minutes, etc. to check for the presence of an undesirable scent. If the module does not detect the presence of an undesirable scent, no action may occur until the next routinely checks the area for an undesirable scent. The olfaction module 145D is not limited to qualitative readings of scents. Quantitative readings can also be realized through spectroscopy (or gas chromatography mass spectrometry) that can be used to identify gas, liquid or solids content. These specific olfactory readings can be processed through a database to alert unsafe conditions that are outside of the traditional definition of smell. Some of the possible safety alert examples are biohazard, chemical identification, radiation levels, etc.

As mentioned above, a sensor 130 may include a camera, video camera, infrared sensor, and/or a voice recognition tool. The action screener 145 may be configured to interpret action(s) received by the camera, video camera and/or voice processing recognition tool (e.g., receiver) 130 from a user in order to generate a response. For example, a user may speak aloud to turn on the television to a particular channel. The projector 130c may subsequently be activated, and through the network 200, begin to project content from the particular channel on to, for example, the wall, floor, or other surface. FIG. 4 illustrates a user in a room with a fixture 100 in communication with a fixture computing device 117. The fixture 100, via projector 130c, is projecting indicia 160 onto the wall, which is viewable by the user.

In embodiments, the action screener 145 may be configured to recognize certain gestures from a user for the purpose of activating various features of the fixture 100. For example, a sensor 130 (e.g., camera or video camera) may be programmed to recognize a particular sequence of movements to activate the projector 130c. Another sequence of movements may be utilized to deactivate the projector 130c. Still another sequence of movements may be utilized to activate another output device 130 via the response generator 145F (e.g., a fragrance dispenser) or a remote module 300, as described in greater detail below. Gesture interactivity is not limited to human interaction. For example, movements of animals, plants, objects, etc. may be used for interactive input to the system in certain embodiments. Gesture monitoring may also extend to behavior observation where gesture movements outside of a dynamic normalized curve can be identified resulting in alert conditions that can be communicated externally as anomalies, pre-alarms, or alarm alerts. An example could be a cashier's anxious behavior during a transaction which could trigger a pre-alarm, which may subsequently progress to a serious alarm condition based on dynamic gestures (e.g., abnormal behavior, pre-trained trigger movements, or deceptive cues).

It shall be understood that fixtures 100 having certain sensors 130 such as cameras and/or video cameras may be undesirable in sensitive locations, such as restrooms, bedrooms, etc. Accordingly, some fixtures 100 may only include sensors 130 which may be acceptable in such locations, such as voice recognition sensors, infrared sensors, etc.

As described briefly above, the response generator 145F may send a request for action over the network 200 to one or more remote modules 300 and 400 in response to receipt of information from the various sensors 130. The module 300 may include other fixtures 100 located within a particular geographic location, or other systems located throughout a building, such as the HVAC system, the security system, sprinkler system, etc. Information received by the sensor(s) 130 may trigger the response generator 145F to send a signal over the network 200 to elicit a controlled response e.g., turning on the heat or A/C, tuning the temperature, etc. from the respective module 300. Here, the memory 135 may be pre-programmed (which may be updated from time to time) with user preferences concerning particular operations around a geographic location, such as preferred temperatures (e.g., at particular time intervals in a particular location), amount of light, audio, etc.

As noted above, the respective module 300, be it an HVAC system, security system, sprinkle system, or other remote system, may be equipped with a network interface and processor for communicating over the network 200 with the fixture computing device 117 for the purpose of receiving instructions from the fixture computing device 117 in response to information received from the one or more sensors 130.

For example, in an embodiment, the fixture 100 may include a thermometer 130 and a voice recognition sensor 130. The thermometer 130 may decipher the temperature in and around a particular location. As the thermometer 130 receives said temperature data, the fixture computing device 117, via the software 140, may determine that the temperature is above (or below, as the case may be) the predetermined desired temperature for that location at that time. The response generator 145F may therefore send a signal to the HVAC system (e.g., module 300), causing the HVAC system to turn up the air conditioner to reduce the temperature at that location. Other modules 300 may additionally be communicatively coupled to the fixture 100, thus allowing the user to control various systems throughout a building from a single location.

In embodiments, the user may additionally, or alternately, control the various modules 300 via voice interaction with the fixture 100. For example, the user may simply speak "turn the temperature to 68" which may be picked up by the voice recognition sensor(s) 130 which may cause the response generator 145F to send a signal to the HVAC system. In some embodiments it will be desirable to pre-process and post-process audio signals for the purposes of understanding speech for interactive inputs as well as overcoming non-ideal acoustical properties such as echoes, noise-profiles (e.g. water based echo patterns within a shower). The system utilizes a closed loop of refining the input and output waveforms of audio speech, music, and ambient noise shaping to provide a seamless interactive experience for the user. These techniques ensure that the functions such as voice processing recognition as well as providing a flat frequency response listening environment. Multiple fixtures 100 may work in conjunction through a distributed network in order to optimize the performance of signal processing algorithms.

The remote module 400 may, in embodiments, be a remote device for controlling the light 110, for example. The remote device may be a cell phone, a laptop computer, a tablet, or any other appropriate device that may be programmed to communicate over the network 200 for the purpose of controlling the system. Such devices are well known to those of skill in the art.

In embodiments, the system includes a plurality of fixtures 100 (and therefore fixture computing devices 117) in communication over the network 200. As a user moves from one location to another, motion sensors 130 in the respective fixtures 100 may detect movement. The fixture computing device 117 in a first location may communicate (e.g., over the network 200) with a fixture computing device 117 in a second location to alert the fixture computing device 117 in the second location of movement of the user such that the user experience is continuous. For example, consider a projector 130c in the first fixture 100 that, via fixture computing device 117, is projecting a TV show at a first location. When the user moves from the first location to a second location, a motion sensor 130 in the fixture 100 in the first location may detect that the user is no longer in the room and shut the projector 130c off. When the user enters a second location, the motion detector 130 in the second fixture 100 may detect same, and the projector 130c in the second fixture 100, via the fixture computing device 117, may be activated to project the TV show in the second location. Thus, the user may experience virtually uninterrupted entertainment as he moves throughout a building. Multiple fixture 100 devices may be operated in conjunction to provide fractional frame projection per fixture 100 in order to project a larger overall perception of projected screen image. In other words, each fixture 100 may project (or provide a portion of) the overall desired resulting image where the plurality of fixture 100 devices provides an overall seamless composite image.

In some embodiments, the fixture computing device 117 is provided together with the fixture 100, and the fixture 100 is disposed in a harsh environment, such as in or near a shower, in a pool, etc. Here, the fixture computing device 117 may be enveloped in a housing so as to protect the various components from water damage.

In embodiments where the fixture 100 is disposed at or near a shower, for example, the projector 130c (via positioning of the housing 105) may be configured to project on a wall or other surface. Alternately, the projector 130c may be configured to project on a pane of glass, such as the shower door. Various systems exist which may allow for the projection of images on panes of glass. Exemplary window panel systems for the projection of image data are described in U.S. patent application Ser. Nos. 14/807,331 and 15/853,079, which are incorporated by reference herein in their entireties. It shall be understood that the projector 130b may be provided in conjunction with speakers 130 such that a user can also hear audio data in addition to the projected image data.

In some embodiments, it may be desirable to project at angles that are not perpendicular in relation from the projector's lens to the projection viewing surface. In these cases it is necessary to utilize a pre-processed optical correction mapping algorithm that can correct for keystone effects which can provide correction to aspect ratio and angular cohesion and framing of the desired projection image. In other embodiments the optical correction mapping algorithm may utilize three-dimensional spatial mapping techniques to allow projection onto surfaces that are either inconsistent in elevation (e.g. not a flat screen) or a contoured 3-dimensional surface such as an object on a table or a person's face. The inverse process of projecting a pre-processed optical correction mapped image yields a corrected image for angle and varying elevation to provide desirable image viewability.

Reference is made herein to a can light which is for use in a structure such as a building. It shall be understood by those of skill in the art, however, that the components described herein may be incorporated into other light fixtures, including but not limited to light fixtures in pools, above showers, street lamps, as part of the fixture for a ceiling fan (FIG. 5). Further embodiments may incorporate fixtures 100 into kitchen counter lighting, backsplash displays, window frames (e.g., in a curtain panel display, such as a display incorporating smart glass), holographic table-to-cup projection, airplane seatbacks, etc.

FIGS. 8A, 8B, 9, and 10 illustrate an alternative embodiment of a fixture 800 for use as a pool light. The fixture 800 is substantially similar to the fixture 100 except as shown and/or described herein, or as would be inherent. Further, those skilled in the art will appreciate that the embodiment 800 may be modified in various ways, such as through incorporating all or part of any of the various described embodiments, for example. For uniformity and brevity, reference numbers between 800 and 899 may be used to indicate parts corresponding to those discussed above numbered between 100 and 199 (e.g., sensor 130 corresponds generally to the sensor 830), though with any noted or shown deviations.

Here, the fixture 800 includes a projector 830b. The projector 830b may be configured to project image data into the pool 700, and optionally, onto the pool floor 705. The fixture 800 may further include one or more sensors and/or output devices 830a and 830c for gathering data at or near the fixture 800. In embodiments, the sensors and/or output devise 830a and 830c may optionally include thermometers, cameras, video cameras, infrared sensor, speaker, pH sensors, chemical detection sensors, etc.

Similar to the fixture 100, the fixture 800 is communicatively coupled to a fixture computing device 817 which may be part of, or remote from, the fixture 800. The fixture computing device 817 may include various functional modes (generally 845), including an action screener 845A, a response generator 845B, a content generator 845C, and an alert generator 845D. The functional modes 845 operate in conjunction with the sensors 830a and 830c to analyze data from the sensors 830a and 830c and to provide a response thereto. In addition, the fixture 800 may be communicatively coupled (e.g., over a network 200) with remote modules 900A and/or 900B for providing a response, as is described herein. It shall be understood that the remote modules 900A and 900B can be multiple modules, each of which may have its own functionality.

The action screener 845A may, for example, be configured to interpret action(s) received by a camera and/or video camera 830 from a user in order to generate a response. In particular, the action screener 845A may be configured to recognize erratic or unsynchronized movements to detect a likelihood of drowning (e.g. dynamic gesture decoded actions). In such an event, the action screener 845A, via the video camera 830, may detect suspicious activity due to the presence of erratic movement within the viewing field. Upon determining that there is a likelihood of suspicious activity, the action screener 845A may activate the alert generator 845D. The alert generator 845D may send out an alert (e.g., wirelessly over the network 200) to a remote device 900A, such as a mobile device. At the same time, the alert generator 845D may cause a remote device 900B, such as a speaker, to provide an audio indication of a possible unsafe situation. Still further, the alert generator 845D may cause the light in the fixture 800 to flash. In this way, persons in the pool and outside of the pool may be alerted to the presence of a potentially unsafe situation.

A user of the remote device 900A, such as a parent or a lifeguard, may assess the situation and interact with the remote device 900A (equipped with the necessary programming) to either deny the presence of an unsafe situation, or to confirm that an unsafe situation is present. The alert generator 845D may include a timer, which gives the user a predetermined period of time to either confirm or deny the presence of an unsafe situation. If the user denies the presence of an unsafe situation, then the alert generator 845D may be deactivated, and the video camera sensor 830 may resume scanning the area for possible unsafe situations. If, instead, the timer expires, or the user confirms the presence of an unsafe situation, then the alert generator 845D may enter into a catastrophic mode.

In the catastrophic mode, the alert generator 845D may activate a remote device 900C, such as a flotation device to the area where the distressed swimmer is located. In an embodiment, the flotation device is a net-like flotation device or pad that is housed at the bottom of the pool. When the catastrophic mode is activated, the net is released from latches at the edge of the pool, and surrounds the distressed swimmer to prevent the swimmer from drowning. In embodiments, the net has a degree of buoyancy that causes the net to float on the water, thereby preventing the swimmer from drowning. In another embodiment, the net may be programmably buoyant. Here, the net or pad may be selectively filled with a gas (e.g., a gas that is lighter than water) via, for example, activation of a firing mechanism by the alert generator 845D. The firing mechanism may pierce a gas cartridge communicatively coupled (e.g., via a tube) to the flotation device. Gas may flow from the cartridge to the flotation device causing the flotation device to inflate. Once the swimmer is safely removed from the pool, the flotation device may be deflated (e.g., via the use of selective openings in the device) and returned to its storage location. In embodiments, latches 910, such as solenoid latches, hoists, or the like, may be utilized to move the flotation device back to its storage position.

Instead of, or in addition to, a video camera 830, the fixture 800 may include a voice processor recognition tool. The voice recognition tool may be specifically configured to recognize sounds (e.g., "HELP!", unusual splash patterns, screams, extended garbled speech, etc.) to activate the action screener 845A and the alert generator 845D, as described herein. In applications such as pool lighting, interactive safety devices will utilize pre- and post-processing with a closed-loop to resolve "safe" and "unsafe" conditions such as a child falling in the pool and calling for help. Closed loop processing techniques for identification, safety, etc. is not limited to audio and can be realized utilizing visual, temperature and other input signals.

Optionally, sensors 830 may additionally be located outside of the pool (e.g., via additional fixtures 800 disposed around the pool such as on light poles, life guard stands, etc., or as a standalone sensor 830). Where a plurality of fixtures 800 are utilized, each of the fixture computing devices 817 is communicatively coupled together, e.g., over the network 200, as is described herein. In embodiments, the action screener 845A may be configured to recognize certain purposeful gestures from a user for the purpose of activating various features of the fixture 800. For example, the sensor 830 (e.g., camera or video camera) may be programmed to recognize a particular sequence of movements to activate alert generator 845D to send an alert to an employee to bring another drink. Gesture interactivity is not limited to human interaction. For example, movements of animals, plants, objects, etc. may be used for interactive input to the system in certain embodiments.

It shall be understood that while the alert generator 845D is described herein as generating alerts due to the perceived presence of an unsafe situation, the alert generator 845D may additionally, or alternately, be configured to provide alerts to a remote module 900A, such as a remote device, for the purpose of providing refreshments to a pool patron.

Figure 6:
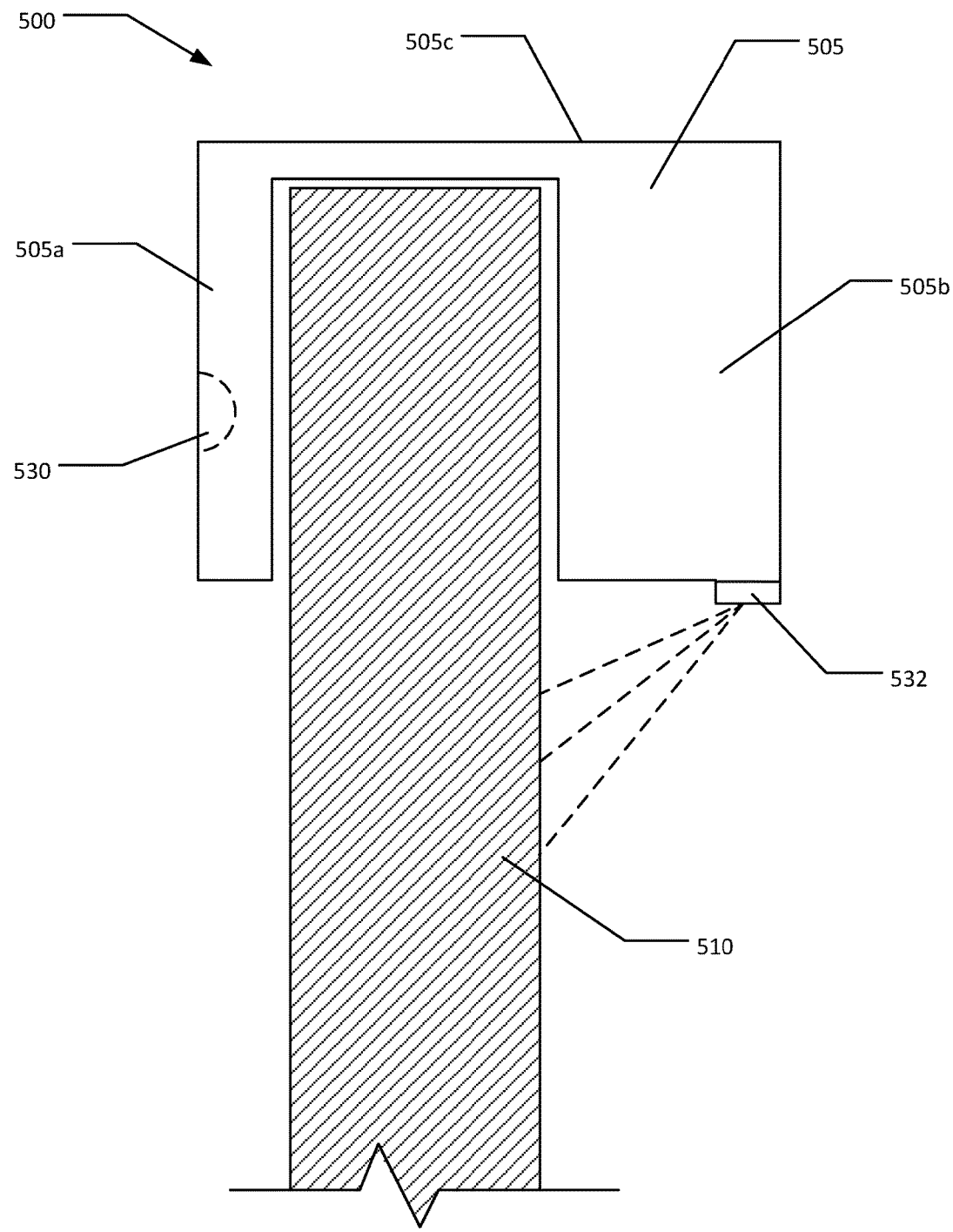
FIG. 6 is a side view of a fixture according to yet another embodiment of the invention.
Figure 7A:
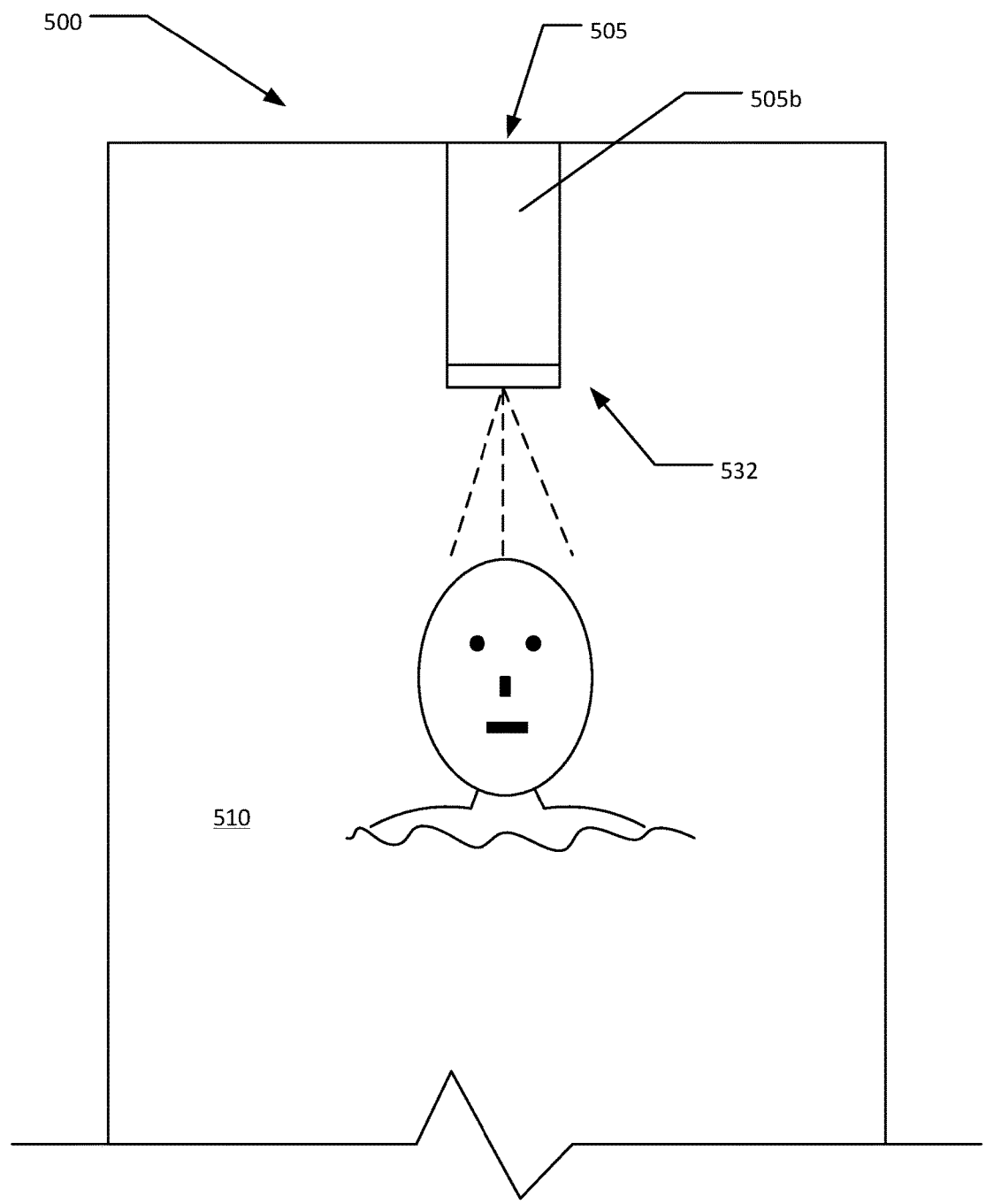
FIG. 7A is a perspective view of a fixture according to still yet another embodiment of the invention.
Figure 7B:
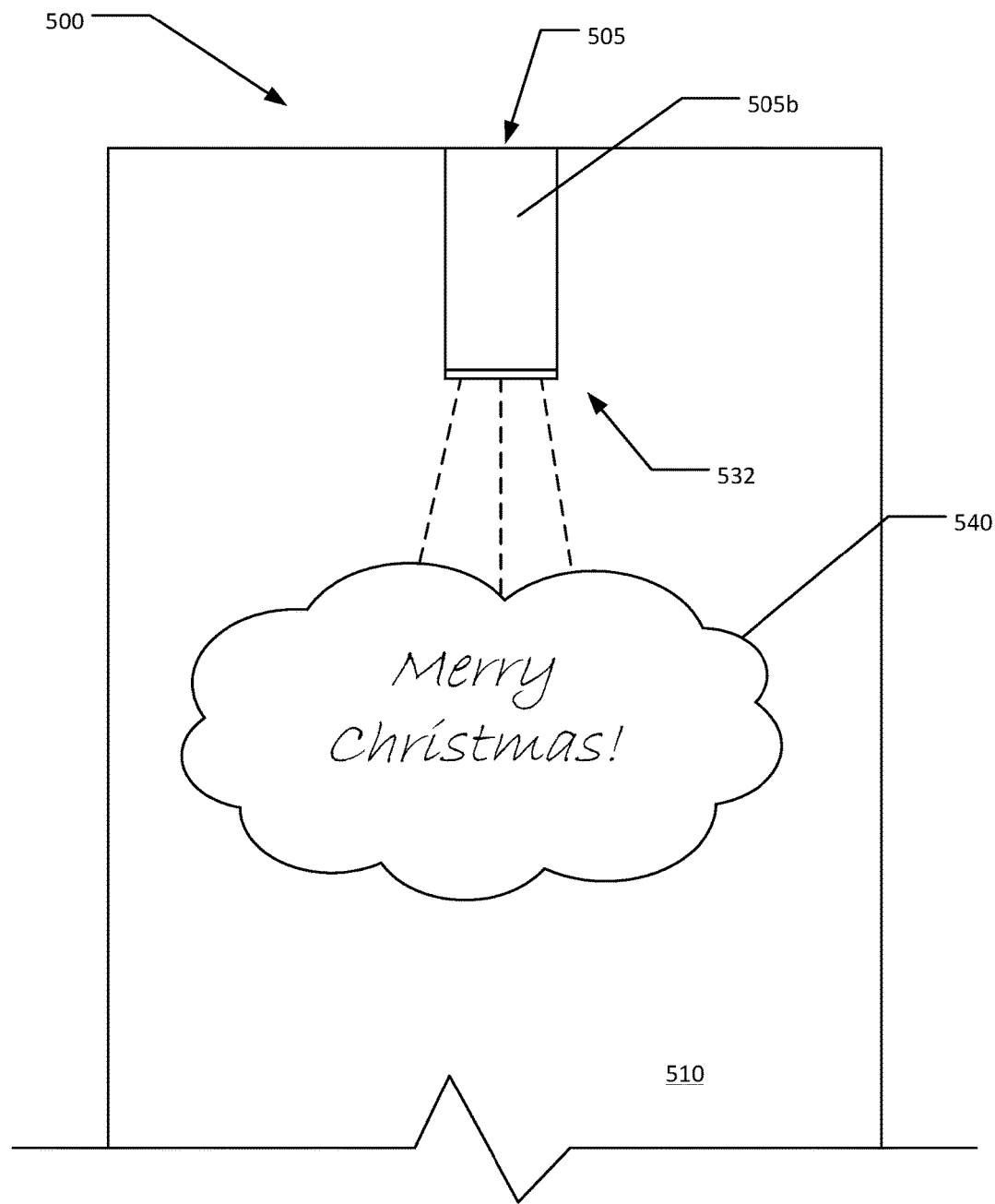
FIG. 7B is a perspective view of a fixture according to a further embodiment of the invention.
Figure 8A:
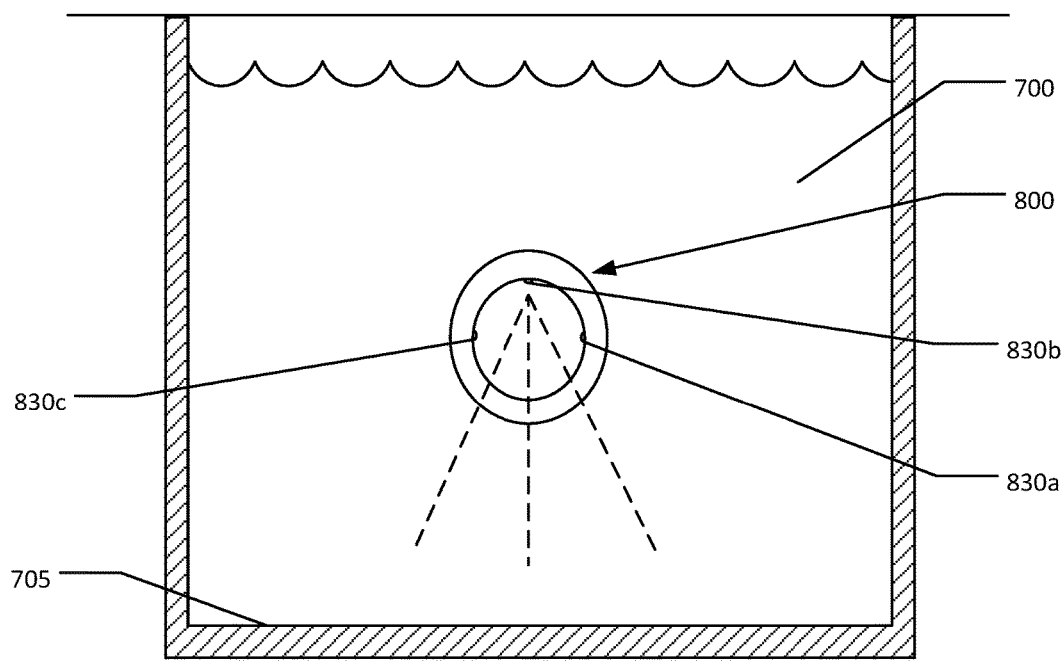
FIG. 8A is a front view of a pool fixture according to another embodiment of the invention.
Figure 8B:
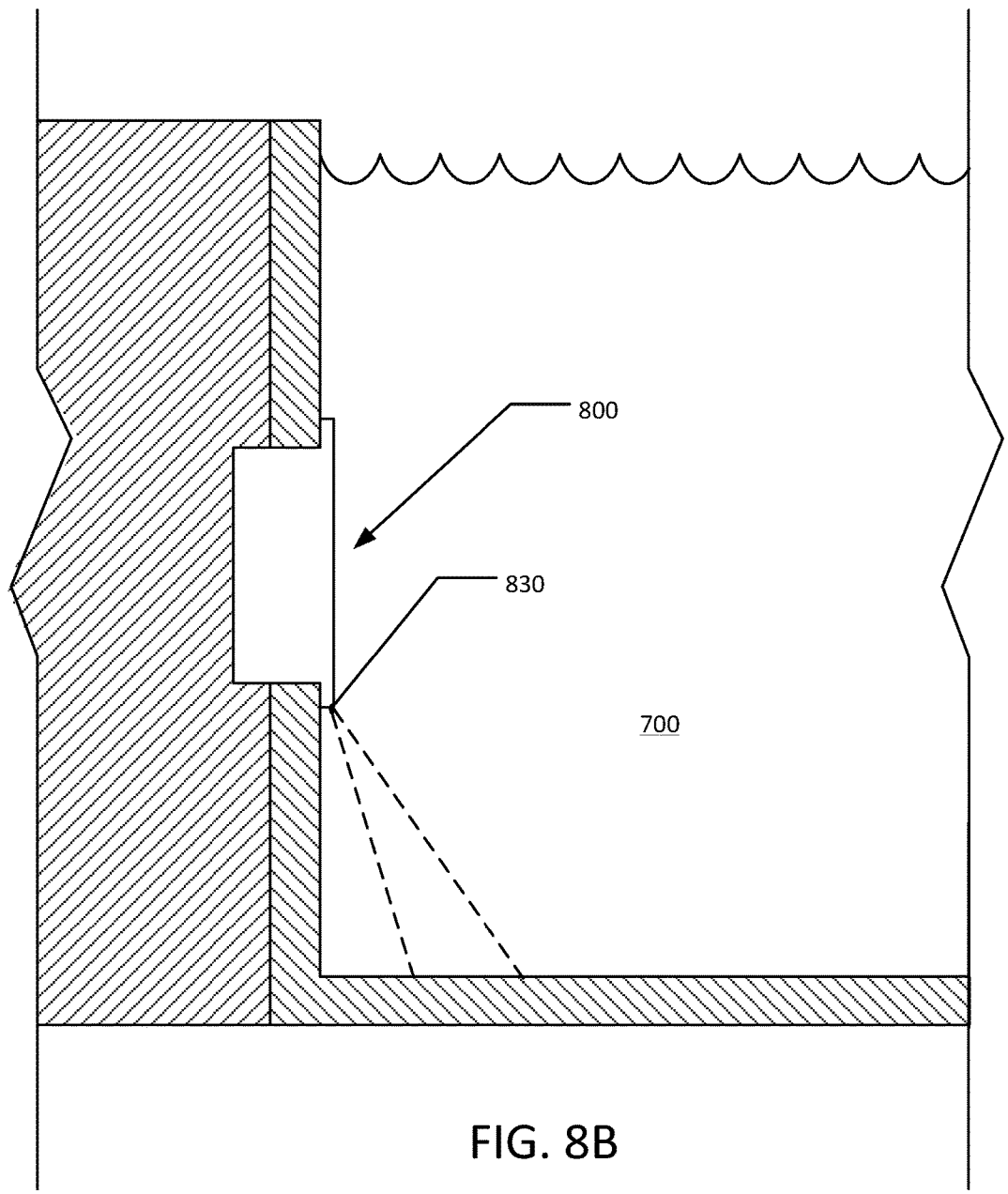
FIG. 8B is a side view of the pool fixture of FIG. 8A.
Figure 9:
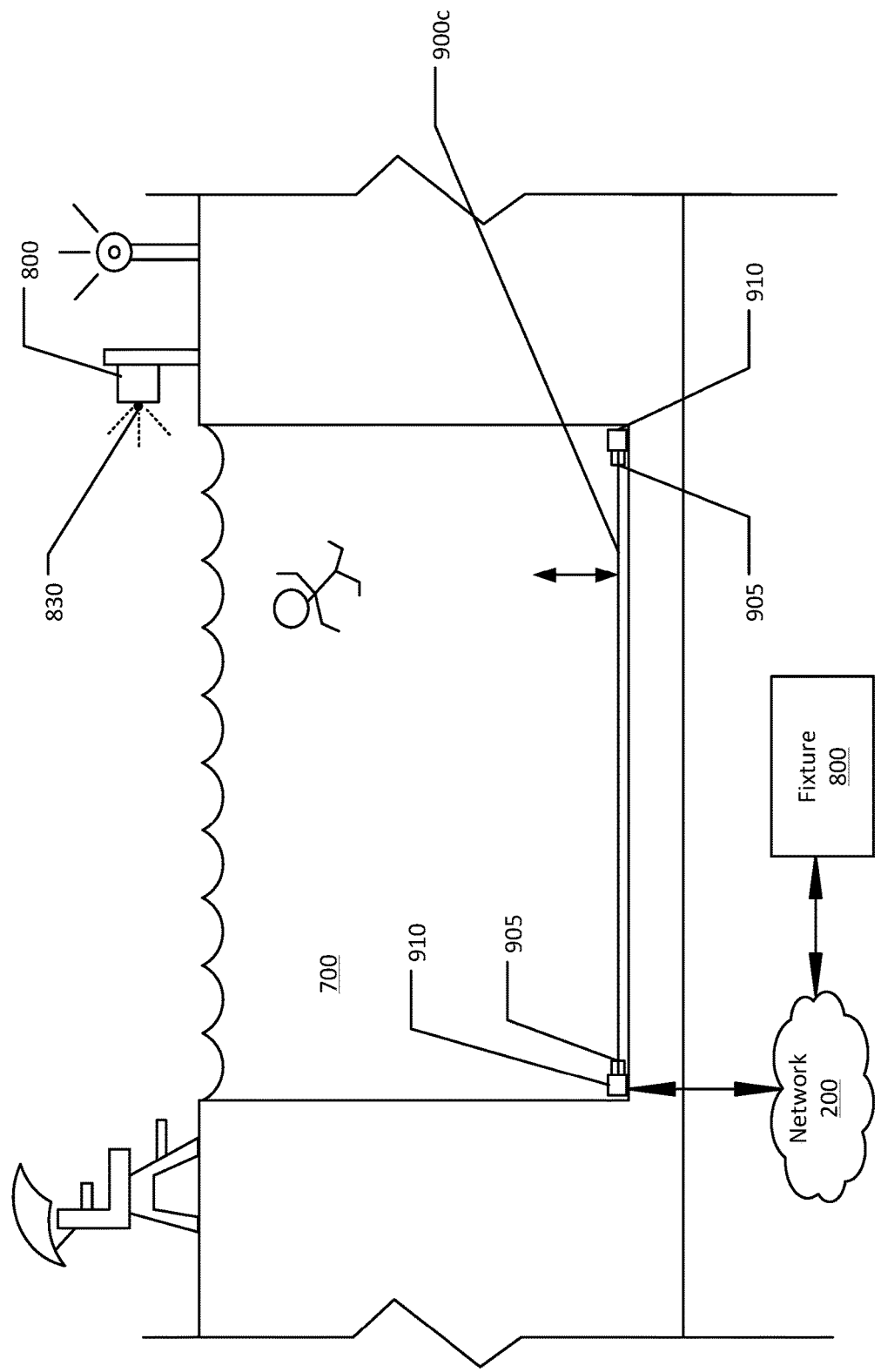
FIG. 9 is a perspective view of system incorporating a pool fixture according to still another embodiment of the invention.
Figure 10:
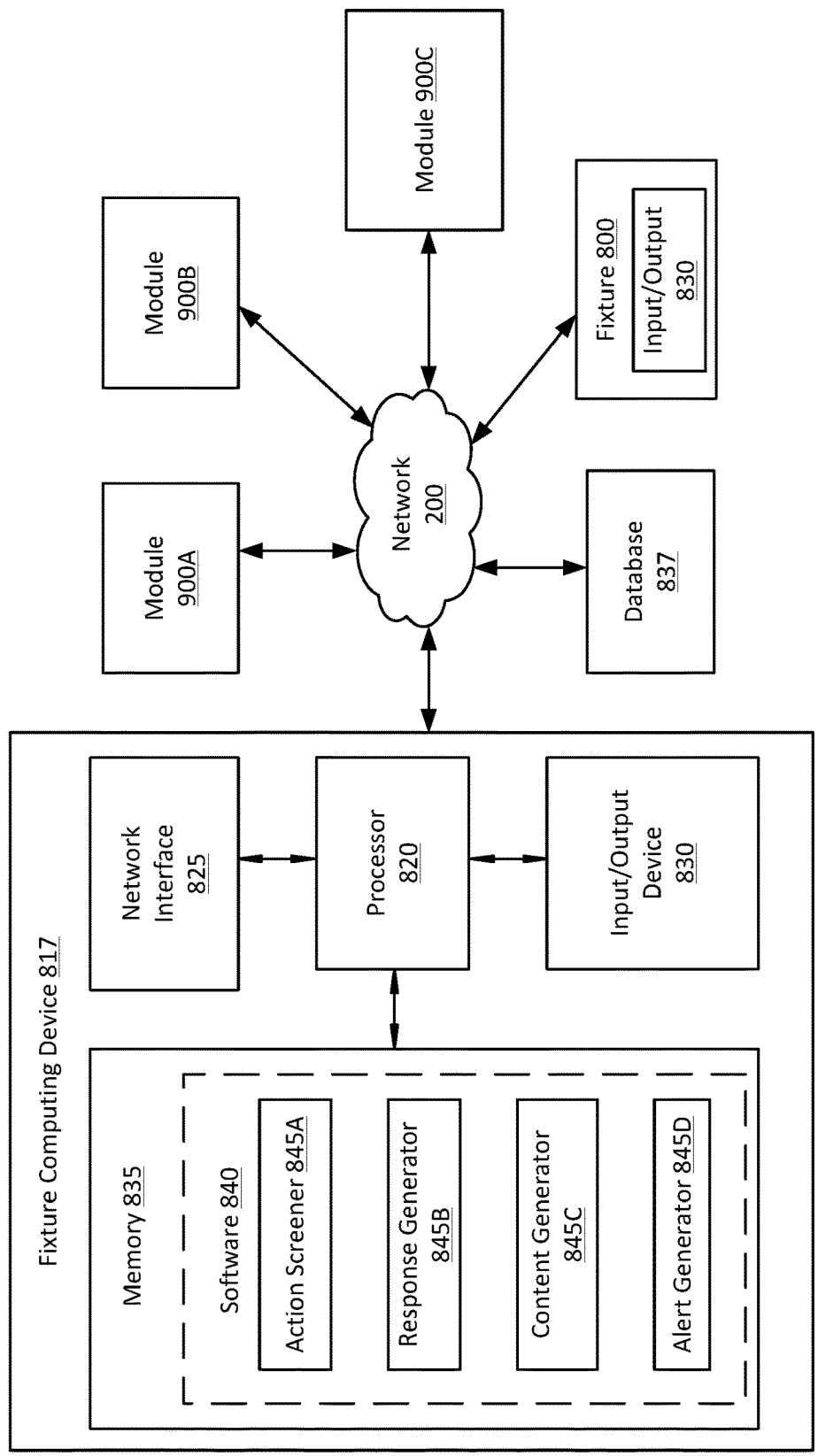
FIG. 10 is a schematic illustration of a system incorporating a fixture according to an embodiment of the invention.

FIGS. 6-7B illustrate another alternative embodiment of a fixture 500 consisting of a hook 505 that fits over, for example, a door 510 (although it may be configured to interact with other appliances, equipment, etc.). Here, the hook 505 has a first appliance engaging portion 505a and a second appliance engaging portion 505b connected via a central portion 505c. In the embodiment shown in FIGS. 6-7B, the first appliance engaging portion 505a is situated on the outside of the door 510 (e.g., facing outside); the second appliance engaging portion 505b is thus situated on the inside of the door 510.

The first appliance engaging portion 505a may be equipped with one or more sensors (generally, 530). The sensors 530 may include but are not limited to video recorders, microphones and/or sound recorders, cameras, temperature gauges, etc. The sensors 530 may optionally be contained inside a housing which may protect the sensors 530 from the elements. In an embodiment, the second engaging portion 505b includes a projector 532. The projector 532 may be configured to be in communication (e.g., wired or wireless, including over a network, WiFi, Bluetooth, cellular, etc.) with the sensors 530 at the first appliance engaging portion 505a.

While the sensors 530 are shown on an outside of the door with the projector 532 on an inside of the door, it shall be understood that sensors 530 may additionally, or alternately, by on the inside of the door (e.g., in the second engaging portion 505b), with the projector 532 additionally, or alternately, on an outside of the door (e.g., in the first engaging portion 505a).

In one embodiment, illustrated in FIG. 7A, the sensor (not visible) is a video camera that is equipped with a microphone. The sensor 530 is in communication with the projector 532. When the sensor 530 detects the presence of an individual in front of the door 510, the individual's likeness may be projected onto the backside of the door 510 such that a person standing in the house may see the individual on the other side of the door. One or more sensors on the second appliance engaging portion 505b, such as a video camera and/or microphone may similarly be configured to record and transmit the likeness of the person standing on the inside to the person standing on the outside via a projection device (e.g., like projector 532).

In another embodiment, illustrated in FIG. 7B, the projector 532 may be configured to project indicia 540 onto the inside of the door 510. The indicia 540 may be selected from a database 137 in the fixture computing device 117 associated with the fixture 500 (which may be accessed wirelessly over the network 200, for example) for projection onto the door 510. In embodiments, the database 137 may be accessed by a wireless device 400 (e.g., a cellular phone) which may allow a user to select the indicia 540 that is to be projected onto the door 510. The projector 532 may be configured to automatically switch between projecting an image from a sensor 530 in the first appliance engaging portion 505a and projecting indicia 540, depending on the information that is being received by the sensor 530. In embodiments where the sensors 530 include sensors for monitoring temperature, humidity, etc., the information may be communicated (e.g., wirelessly) to the user or other subsystems which may be distributed throughout the home as discussed herein.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention. Further, it will be understood that certain features and subcombinations are of utility and may be employed within the scope of the disclosure. Further, various steps set forth herein may be carried out in orders that differ from those set forth herein without depart from the scope of the present methods. This specification shall not be restricted to the above embodiments.

Any units of measurement provided herein are exemplary in nature only and are not meant to specifically define the dimensions of the system. Other dimensions may be appropriate or desirable.

The invention claimed is:

1. A fixture system, comprising:
   a mobile device communicatively coupled to the fixture;
   a fixture, comprising:
      a first sensor for determining a proximity of the mobile device to the fixture; and
      a first output device; and
   a computing system comprising a processor and non-transitory computer memory comprising instructions that, when executed by the processor, perform the following steps:
      (a) determine, via the first sensor, that the mobile device is within a predetermined proximity threshold; and
      (b) activate an output via the first output device;
   wherein the output is user-specific content, and wherein the user specific content is generated based on a user profile stored in the computer memory.

2. The fixture system of claim 1, wherein the fixture is configured as one of: a light, a speaker, and a smart glass display.

3. The fixture system of claim 1, wherein the fixture further comprises an input device selected from the list consisting of: a motion detector, a thermometer, a camera, a video camera, a proximity sensor, a voice processor, and an infrared detector.

4. The fixture system of claim 3, wherein the remote device is selected from the list consisting of: a light, an HVAC system, and a security system.

5. The fixture system of claim 3, further comprising a second output device, wherein the second output device initiates an output based on information from the input device.

6. The fixture system of claim 5, wherein the second output device is selected from a list consisting of: a light, a speaker, a fan, and a smart glass display.

7. The fixture system of claim 1, further comprising a remote device communicatively coupled to the computing system, wherein the programming further comprises instructions that, when activated by the processor, perform the following steps:
   (c) activate the remote device when the mobile device is within the predetermined proximity threshold.

8. The fixture system of claim 7, wherein the programming further comprises instructions that, when activated by the processor, perform the following steps:
   (d) send an alert to the mobile device confirming the activation of the remote device.

9. The fixture system of claim 1, wherein the output device is selected from the list consisting of: a speaker, a projector, and a fragrance delivery system.

10. The fixture system of claim 1, further comprising a second output device.

11. The fixture system of claim 10, wherein the second output device is selected from a list consisting of: a light, a speaker, a fan, and a smart glass display.

12. The fixture system of claim 10, wherein the second output device is activated by the mobile device.

\* \* \* \* \*